United States Patent [19]
Baden

[11] Patent Number: 5,658,311
[45] Date of Patent: Aug. 19, 1997

[54] HIGH PRESSURE EXPANDER BUNDLE FOR LARGE DIAMETER STENT DEPLOYMENT

[75] Inventor: Jeannine B. Baden, Wayzata, Minn.

[73] Assignee: Schneider (USA) Inc., Minneapolis, Minn.

[21] Appl. No.: 675,862

[22] Filed: Jul. 5, 1996

[51] Int. Cl.$^6$ .......................... A61M 37/00; A61M 29/00
[52] U.S. Cl. ........................ 606/192; 604/95; 604/96; 604/101; 604/192; 606/194
[58] Field of Search .................... 604/95–96, 104; 606/7, 191–200; 128/207.14, 207.15

[56] References Cited

U.S. PATENT DOCUMENTS

| Re. 34,327 | 7/1993 | Kreamer . |
|---|---|---|
| 4,141,364 | 2/1979 | Schultze . |
| 4,406,656 | 9/1983 | Hattler et al. . |
| 4,580,568 | 4/1986 | Gianturco . |
| 4,581,017 | 4/1986 | Sahota . |
| 4,655,771 | 4/1987 | Wallsten . |
| 4,733,665 | 3/1988 | Palmaz . |
| 4,739,762 | 4/1988 | Palmaz . |
| 4,787,388 | 11/1988 | Hofmann . |
| 4,886,062 | 12/1989 | Wiktor . |
| 5,037,392 | 8/1991 | Hillstead . |
| 5,041,126 | 8/1991 | Gianturco . |
| 5,102,417 | 4/1992 | Palmaz . |
| 5,192,307 | 3/1993 | Wall . |
| 5,266,073 | 11/1993 | Wall . |
| 5,270,086 | 12/1993 | Hamlin . |
| 5,308,323 | 5/1994 | Sogawa et al. . |
| 5,403,280 | 4/1995 | Wang . |
| 5,458,575 | 10/1995 | Wang . |
| 5,478,319 | 12/1995 | Campbell et al. . |
| 5,501,667 | 3/1996 | Verduin, Jr. . |
| 5,505,702 | 4/1996 | Arney . |
| B1 4,739,762 | 1/1994 | Palmaz . |

OTHER PUBLICATIONS

Roubin, Gary "Post-Stenting High Pressure Balloon Dilation Strategies", Flex-Stent Focus, vol. 3, Sep. 1995, pp. 3–5.

Schneider Brochure entitled "Valvuloplasty Dilation Catheters Monofoil™, Bifoil™, Trefoil-Meier™", dated Nov. 1988.

Primary Examiner—Michael Buiz
Assistant Examiner—Nancy Connolly Mulcare
Attorney, Agent, or Firm—Haugen and Nikolai, P.A.

[57] ABSTRACT

A balloon catheter includes an inflatable expander member for deploying a large diameter stent includes a plurality of balloon segments affixed to the distal end of a multi-lumen catheter body, the segments being selectively expansible in groups whereby the stent can be spread to conform to the blood vessel in which it is deployed while still permitting blood to perfuse through the spaces occupied by the uninflated ones of the segments. By using plural segments of smaller effective diameter, the composite expander can be made large enough to spread a collapsed stent without exceeding the burst strength of the individual balloon segments.

23 Claims, 3 Drawing Sheets

HIGH PRESSURE EXPANDER BUNDLE FOR LARGE DIAMETER STENT DEPLOYMENT

BACKGROUND OF THE INVENTION

I. Field of the Invention

This invention relates generally to intravascular balloon catheters, and more particularly to a balloon catheter having a plurality of separately inflatable expander segments at a distal end thereof for positioning and deploying relatively large diameter stents.

II. Discussion of the Prior Art

It is known in the art to use a balloon catheter to deploy nonself-expanding stents as well as post extension of self-expanding stents within the vascular system. For the most part, stenting has been used in balloon and laser angioplasty procedures to provide reinforcement to a vessel wall. In such procedures, a compressed metal or plastic stent is positioned concentrically over a deflated expander member on the distal end of a catheter. The catheter is then introduced into the patient using the Seldinger technique and advanced through the vascular system until the expander member and stent are located at a desired site. By inflating the expander member, the stent is also expanded to a predetermined diameter determined by the O.D. of the inflated expander member. When the expander member is again deflated, the catheter can be withdrawn, leaving the expanded stent in place.

Those skilled in the art appreciate that as the diameter of the expander member increases, the burst strength of that expander member decreases. Thus, while a PET balloon of a 4 mm outside diameter can readily be inflated to 235 psi, larger diameter balloons, say 12 mm in diameter, may only be pressurized to about 100 psi without exceeding its burst strength.

A need exists for a balloon catheter capable of deploying relatively large diameter stents in peripheral blood vessels. As used herein, "peripheral" means any blood vessel external to the heart, including the aortic arch. For example, when attempting to treat abdominal aorta aneurisms (AAA), provision needs to be made for expanding a stent having a I.D. of about 12-40 mm depending on the sex and age of the patient. A balloon catheter having a single expander member of that size necessarily dictates that a lower pressure be used to avoid exceeding the burst pressure of the expander member. Thus, the lower pressure may be insufficient to expand the stent that is to be used in treating the AAA condition.

Another drawback of existing large diameter balloons, especially those fabricated from PET is their tendency towards "winging". When such a balloon is inflated and subsequently deflated prior to withdrawing the catheter, the deflated balloon tends to collapse in a form exhibiting flat wing-like projections extending radially from the catheter body. The effective O.D. of the wing plane can exceed the original O.D. of the fully inflated balloon. The presence of these wings makes it difficult to withdraw the catheter into its associated guide catheter and, additionally, may dislodge the otherwise secured stent graft during balloon withdrawal. U.S. Pat. No. 5,037,392 addresses this problem.

Accordingly, it is principal purpose of the present invention to provide an improved stent delivery catheter for use with relatively large diameter (5-50 mm) stents which can be inflated to a sufficiently high pressure to expand stents of this size without exceeding the burst strength of the balloon and which can be deflated without significant winging.

It has been previously established that the longer a balloon is inflated against a stenosis the better the patency result. However, it is also known that the longer downstream tissues are deprived of blood the more severe the resultant ischemia. During procedures involving stenosis and aneurisms in the aorta, for example, it is necessary to allow large volumes of blood to continue to pass beyond the worksite to the lower abdomen and into the legs. Failure to do so results not only in deprivation of blood to the lower extremities but also in a pressure build-up which when relieved (as in during withdrawal of the apparatus) can and has washed the stent graft, which had just been carefully placed, downstream and out of the physician's control, posing a risk to the patient, and further lengthening the procedure while the physician attempts to reposition the device.

Another problem that currently exists is the blockage of air into the lungs while balloon expanding a stent in the trachea, the right or the left bronchus.

Depending on the complexity and duration of the procedure, these aforementioned blockages of blood and air present substantially undesirable risks associated with much of the existing art currently in use to perform these types of interventions.

There are several inventions currently available which have attempted to address the need for perfusion of bodily media beyond the lesion site by bundling several balloons together however the result is only partially successful. Their limitations lie in the fact that perfusion is accomplished only because the bundled balloons create a "default orifice" between the junction of the outside radiuses of the circular balloons. These "default orifices" are relatively small and substantially restrict the volume of media which could pass through them. Furthermore, these "default orifices" being small could become clogged, completely stopping media passage altogether.

The present invention allows significantly larger volumes of media to pass beyond the lesion by deliberately forming the balloons into pie-shaped wedges which when assembled and connected to a fluid source can be selectively inflated or deflated either individually, simultaneously or in alternating groups. The concept of simultaneous inflation and deflation of alternating balloon members allows anchoring and expansion of the graft or stent while simultaneously allowing large quantities of blood or other media to pass.

There are conceivably other uses for a large diameter, high pressure, alternating cyclic expander member than so far mentioned. Conceivably, the inflation and deflation of alternating balloons could be cycled to match the pulsing of blood or the rhythm of breathing. One use may be as an interventional pump if there were a need to pump a dislodged device or mass of a biological nature either up or down stream.

If the diameter of the alternating balloons was varied between large and small, another use of the concept of separate balloon group inflation could be to expand two different stent graft diameters in different locations without withdrawal and exchange for another balloon size. In this scenario, it may be necessary to rotate the device such that all areas of the stent, graft, stenosis, etc. are uniformly dilated since only alternating balloons have the same effective diameter.

SUMMARY OF THE INVENTION

The foregoing shortcomings of the prior art are overcome in accordance with the present invention by providing a new and improved balloon catheter for deploying larger diameter stents in peripheral blood vessels. In accordance with the present invention, the balloon catheter comprises an elongated, flexible tubular catheter body member of generally circular cross-section and having a proximal end, a distal end and a plurality of lumens extending from the proximal end to the distal end. The catheter body member includes a plurality of inflation ports extending radially through the wall of the catheter body member proximate a distal end thereof and these inflation ports communicate with at least of the plurality of lumens in the tubular catheter body member. Affixed to the wall of the catheter body member proximate the distal end thereof is an expander member that comprises a plurality of elongated, tubular, extensible balloon segments which, when inflated, are generally wedge shaped in cross-section and each spans a predetermined arc of the generally circular periphery of the tubular catheter body member. Collectively, the plural inflated segments define a composite expander member having a smooth, generally circular, outer periphery. The balloon catheter further includes a means for placing one of the plurality of inflation ports in fluid communication with the interior of selected ones of the plurality of wedge-shaped balloon segments and another of the plurality of inflation ports in fluid communication with the interior of other selected ones of the plurality of wedge-shaped balloon segments. In this fashion, first and second groups of the wedge-shaped segments can be selectively inflated and deflated, either simultaneously or sequentially, by injecting and removing an inflation fluid into and from one or more of the plurality of lumens.

The individual wedge-shaped segments may be fabricated from PET, PE, nylon, polyvinyl chloride, latex rubber, polyamide, polyurethane, depending upon whether a non-compliant, compliant or semi-compliant expander member is desired.

By selectively inflating and deflating individual balloon segments, it is possible for blood to perfuse past the treatment site through the space associated with the deflated segments.

In that each individual balloon segment is of a smaller effective diameter than the O.D. of the composite expander member, higher burst pressures are achievable and winging is minimized.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
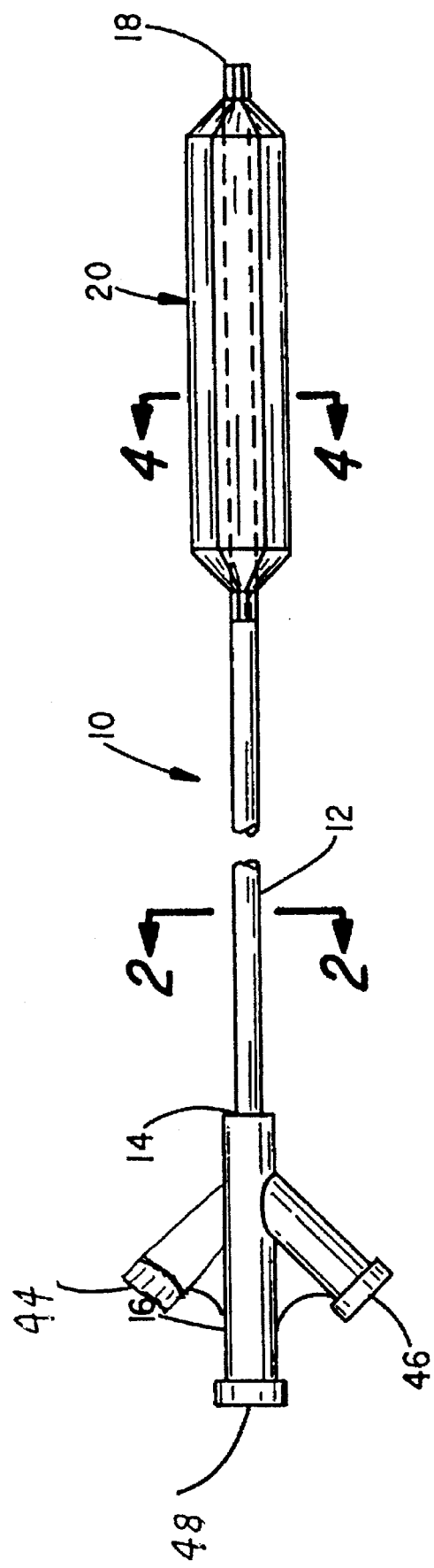
FIG. 1 is a side elevation view of a balloon catheter constructed in accordance with the present invention.

Referring to FIG. 1, there is indicated generally by numeral 10 a stent delivery catheter constructed in accordance with the present invention. The catheter 10 is seen to comprise an elongated, flexible, tubular catheter body member 12 which may be extruded from a variety of thermoplastic materials including, but not limited to, polyester, nylon, polyurethane, PVC, PEBAX, polyimide, and the like. Affixed to a proximal end 14 of the catheter body is a molded plastic hub 16. Joined to the distal end 18 of the catheter body is an expander member indicated generally by numeral 20.

Figure 2:
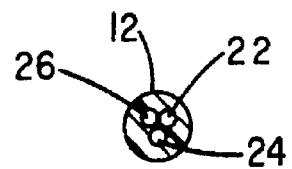
FIG. 2 is a cross-sectional view taken through the catheter's tubular body along the line 2—2 in FIG. 1.
Figure 3:
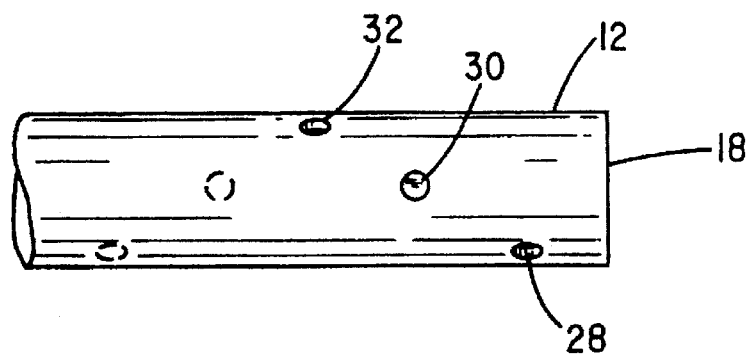
FIG. 3 is an enlarged partial view of the distal end portion of catheter body.

As is indicated by the cross-sectional view of FIG. 2, the catheter body 12 includes a plurality of lumens 22, 24 and 26 running substantially the entire length of the catheter body. FIG. 3 is a greatly enlarged cross-sectional view of a distal end portion of the multi-lumen tubular body 12 that supports the expander member 20 thereon. As can be seen in FIG. 3, arranged symmetrically about the circumference of the tubular body 12 in the area thereof occupied by the expander member 20 are a plurality of inflation ports as at 28, 30 and 32 which extend through the wall of the member 12 to intersect with individual ones of the lumens 22, 24 and 26. In the view of FIG. 3, the expander member 20 is absent to better illustrate the presence of the inflation ports.

Figure 4:
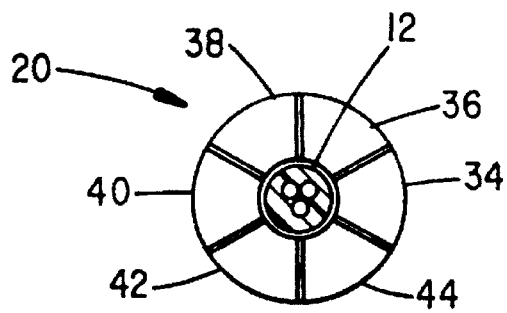
FIG. 4 is a cross-sectional view taken through the expander member along lines 4—4 in FIG. 1.
Figure 7:
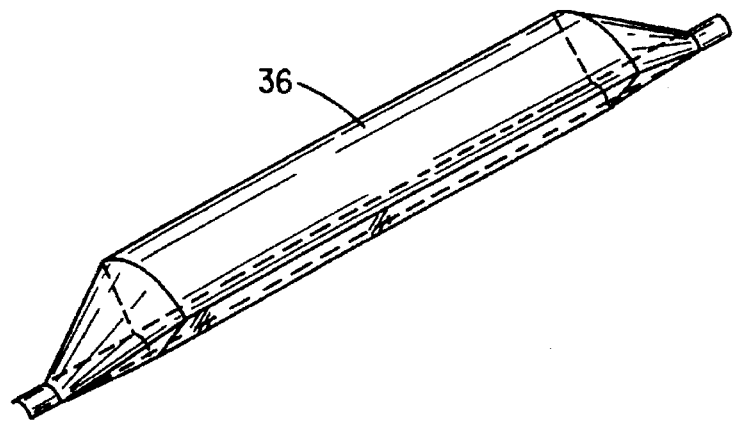
FIG. 7 is an enlarged perspective view of one of the plurality of wedges comprising the catheter's expander member.

Next, with reference to FIG. 4, it can be seen that the composite expander member 20 comprises a plurality of individual segments 34-44, one of which (segment 36) is illustrated in the perspective view of FIG. 7. The individual segments are preferably formed from a plastic parison in a stretch/blow-molding operation so that the thermoplastic material comprises a biaxially oriented film. If a non-compliant expander segment is desired, PET plastic is a good choice. Where a compliant expander member is desired, polyethylene plastic may be used. Nylon is a good choice where a semi-compliant expander is desired. Following the teachings of the Hamlin Pat. No. 5,270,086, an expander member with especially tailored properties can be realized.

Figure 5:
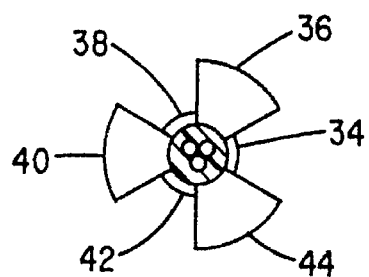
FIG. 5 is a cross-sectional view like that of FIG. 4 but with alternate wedges deflated.

With continued reference to FIGS. 4 and 5, it can be seen that the individual segments 34-44 have a generally wedge-shaped cross-section with a rounded outer exterior wall tapering down to a likewise rounded interior wall of reduced diameter so as to generally correspond to an arcuate surface of the catheter body 12. Opposite ends of the balloon segment 36 are outwardly and downwardly tapered.

A plurality of such segments may be individually bonded to the outer wall of the catheter body 12 and positioned such that one of the inflation ports 28-32 is in fluid communication with the interior of each of the plural segments 34-44. Bonding techniques similar to those currently used in fabricating angioplasty balloons can be used to secure the individual segments to the catheter body 12.

While the cross-sectional view of FIG. 4 illustrates six segments bonded to the catheter body 12, it is appreciated that a fewer number, e.g., four, may be used as well.

In implementing a catheter for deploying a large diameter stent such as those used in treatment of AAA, the catheter body 12 will typically be 16 Fr. in size. Then, assuming that each individual expander segment 36 is approximately 8 mm from its inner wall to its outer wall, the resulting balloon catheter would have a outside diameter of over 21 mm and would typically provide a burst strength of about 300 psi.

The hub 16 on the proximal end 14 of the catheter body 12 is seen to include at least two inflation fluid inlet ports 44 and 46 which are adapted for connection to syringe pumps (not shown) whereby the inflation fluid under pressure may be injected and subsequently extracted. The fluid inlet port 44 may be in fluid communication with one of the plural lumens 22, 24 or 26 while the inlet port 46 is in fluid communication with a different one of those lumens. In this fashion, the expander segments 34-44 can be selectively inflated and deflated. For example, let it be assumed that alternate ones of the inflation ports 28, 30, 32, etc. are in fluid communication with the lumens 22 and 24 and with alternate segments 34-44 of the expander member 20. If inflation fluid is injected into both of the hub ports 44 and 46, simultaneously, all of the expander member segments can be inflated which is the condition represented in FIG. 4 of the drawings. 48 shows an entry port for a guidewire lumen. Now, by extracting the inflation fluid, via only one of the lumens 22 or 24, alternate segments of the expander member will be deflated, yielding a cross-sectional view like that of FIG. 5. Here, blood would be able to perfuse through the spaces between adjacent inflated segments. While the view of FIG. 5 shows segments 36, 40 and 44 being inflated, by extracting the inflation fluid from those segments and simultaneously or subsequently inflating segments 34, 38 and 42 on an alternating basis, the stent being delivered will be uniformly expanded while still permitting blood to perfuse through the space between adjacent inflated segments.

Figure 6:
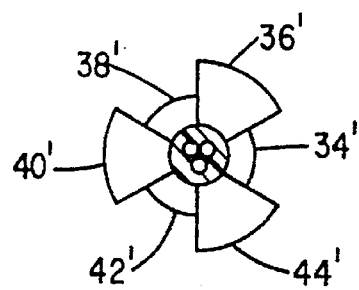
FIG. 6 is a cross-sectional view like that of FIG. 4, but with alternate wedges of a different radial dimension when inflated.

FIG. 6 is a cross-sectional view similar to those of FIGS. 4 and 5, but illustrating a further embodiment in which alternate balloon segments are of differing radii. Here, segments 36' and 40' and 44' are of a radius larger than that of segments 34', 38' and 42' when inflated. This construction can be used to expand two different stent graft diameters in different locations without the need to withdraw and exchange catheters for another balloon size. By simply deflating the larger radius segments while inflating the smaller radius segments, a smaller diameter stent graft can be expanded into place in the target blood vessel. Because of the resulting gap between adjacent segments, it may be necessary to rotate the catheter to thereby address the entire stent I.D. surface.

A further advantage of utilizing a segmented expander member as described herein is that in the event a stent punctures one of the segments, the remaining segments will maintain their pressures and permit the physician to finish the procedure without having to do a catheter exchange at a critical time.

I claim:

1. A balloon catheter for deploying larger diameter stents in peripheral blood vessels, comprising:
    (a) an elongated, flexible, tubular catheter body member of generally circular cross-section and having a proximal end, a distal end and a plurality of lumens extending from the proximal end to the distal end, the catheter body member including a plurality of inflation ports extending radially through a wall of the catheter body member proximate a distal end thereof and communicating with at least one of the plurality of lumens;
    (b) an expander member affixed to the wall of the catheter body member proximate the distal end thereof, the expander member comprising a plurality of elongated tubular extensible segments which, when inflated, are generally wedge shaped in cross-section and each span a predetermined arc of the generally circular cross-section of the catheter body member and collectively define a smooth, generally circular outer periphery of the expander member and
    (c) means for placing one of the plurality of inflation ports in fluid communication with the interior of selected ones of the plurality of extensible segments and another of the plurality of inflation ports in fluid communication with the interior of other selected ones of the plurality of extensible segments whereby first and second groups of the extensible segments can be selectively inflated and deflated either simultaneously or sequentially by injecting and removing an inflation fluid into and from the at least one of the plurality of lumens.

2. A balloon catheter for deploying larger diameter stents in peripheral blood vessels, comprising:
    (a) an elongated, flexible, plastic tubular body member having a proximal end, a distal end and first and second lumens extending substantially the entire length thereof;
    (b) a segmented expander member having a plurality of separate inflatable compartments and a generally circular cross-section, the expander member being affixed to the body member proximate the distal end thereof such that the inflatable compartments concentrically surround the body member; and
    (c) means for selectively injecting an inflation fluid into the first and second lumens for either simultaneous inflation of the plurality of compartments or inflation of any selected ones of the plurality of compartments.

3. The balloon catheter as in claim 2 wherein the expander member comprises a substantially non-compliant thermoplastic material.

4. The balloon catheter as in claim 3 wherein the non-compliant thermoplastic material comprises a biaxially oriented polyethylene terephthalate.

5. The balloon catheter as in claim 2 wherein the plurality of individually inflatable compartments are pie-shaped in cross-section and disposed adjacent one another to form the smooth generally circular periphery when simultaneously inflated.

6. The balloon catheter as in claim 5 wherein the individually inflatable compartments comprise stretch blow-molded plastic film tubes of a predetermined wall thickness and capable of being pressurized to at least 16 atmospheres without exceeding the burst strength of the film tubes.

7. The balloon catheter as in claim 6 wherein the O.D. of the smooth cylindrical surface is in the range of from at least 12 mm to at least 40 mm.

8. The balloon catheter as in claim 1 wherein the body member with the segmented expander member affixed to it is dimensioned to pass through at least a 16 Fr opening when uninflated.

9. The balloon catheter as in claim 2 wherein a gap is created between adjacent inflated ones of the plurality of compartments upon inflation of only selected ones of the plurality of compartments, such that blood may perfuse through the gap as a stent is being deployed in the peripheral blood vessel.

10. The balloon catheter as in claim 2 wherein the means for selectively injecting an inflation fluid into the first and second lumens for inflating the plurality of compartments includes an inflation port extending radially in the catheter body to intersect one of the first and second lumens, the inflation port being in fluid communication with at least one of the plurality of compartments.

11. The balloon catheter as in claim 5 wherein the plurality of pre-shaped inflatable compartments are separately formed and individually affixed to the body member.

12. The balloon catheter as in claim 5 wherein the plurality of individually inflatable compartments are formed as a unitary expander member.

13. The balloon catheter as in claim 2 wherein adjacent ones of the plurality of individually inflatable compartments are of different radii.

14. The balloon catheter as in claim 3 wherein the non-compliant thermoplastic material is selected from polyethylene, polyester, nylon, polyvinyl chloride, latex rubber, polyamide, polyurethane, polyimide, and PEBAX.

15. The balloon catheter as in claim 6 wherein the O.D. of the smooth cylindrical surface is in the range of from at least about 5 mm to at least about 50 mm.

16. The balloon catheter as in claim 15 wherein the O.D. of the smooth cylindrical surface is in the range of from at least about 20 mm to at least about 40 mm.

17. The balloon catheter as in claim 1 wherein the body member with the segmented expander member affixed to it is dimensioned to pull through at least an 8 Fr. sheath or other opening when uninflated.

18. The balloon catheter as in claim 17 wherein the body member with the segmented expander member affixed to it is dimensioned to pull through at least a 14 Fr. guide catheter when uninflated.

19. The balloon catheter as in claim 2 further comprising a stent associated with the catheter, the stent adapted to be at least partially expanded by the segmented expander member.

20. The balloon catheter as in claim 19 wherein the stent is mounted on the expander member.

21. The balloon catheter as in claim 20 wherein the stent is a balloon expandable stent.

22. The balloon catheter as in claim 19 wherein the stent is a braided self-expanding stent.

23. A balloon catheter comprising:

(a) an elongated, flexible, plastic tubular body member having a proximal end, a distal end and first and second lumens extending substantially the entire length thereof, and (b) a segmented expander member having six inflatable compartments, the expander member being affixed to the body member proximate the distal end thereof such that the inflatable compartments concentrically surround the body lumen, wherein the six inflatable compartments are pie-shaped in cross-section and each span a predetermined arc of the tubular body member and they are disposed adjacent one another to form a smooth generally circular periphery which is at least about 5 millimeters in diameter when simultaneously inflated, the compartments capable of being pressurized to at least 16 atmospheres without exceeding the burst strength of the compartments.

* * * * *

UNITED STATES PATENT AND TRADEMARK OFFICE
CERTIFICATE OF CORRECTION

PATENT NO. : 5,658,311
DATED : August 19, 1997
INVENTOR(S) : Jeannine B. Baden

It is certified that error appears in the above-indentified patent and that said Letters Patent is hereby corrected as shown below:

(Claim 2) Col. 6, line 21, after "member" insert -- and each span a predetermined arc of the generally circular cross-section of the catheter body member and collectively define a smooth, generally circular outer periphery of the expander member --.

Signed and Sealed this

Ninth Day of December, 1997

*Attest:*

BRUCE LEHMAN

*Attesting Officer*   *Commissioner of Patents and Trademarks*